US012775028B2

(12) United States Patent
Loccia et al.

(10) Patent No.: US 12,775,028 B2
(45) Date of Patent: Oct. 27, 2026

(54) CURRENT SENSE CIRCUIT AND CURRENT SENSING METHOD THAT ADJUSTS A START MEASUREMENT VALUE FOR SUCCESSIVE MEASUREMENT CYCLES

(71) Applicant: Infineon Technologies AG, Neubiberg (DE)

(72) Inventors: Giuseppe Loccia, Padua (IT); Stefano Orlandi, San Bonifacio (IT); Davide Dal Bianco, Schio (IT)

(73) Assignee: Infineon Technologies AG, Neubiberg (DE)

( * ) Notice: Subject to any disclaimer, the term of this patent is extended or adjusted under 35 U.S.C. 154(b) by 187 days.

(21) Appl. No.: 18/737,744

(22) Filed: Jun. 7, 2024

(65) Prior Publication Data

US 2025/0020700 A1 Jan. 16, 2025

(30) Foreign Application Priority Data

Jul. 12, 2023 (DE) ........................ 102023118449.0

(51) Int. Cl.

| | |
|---|---|
| ***G01R 19/00*** | (2006.01) |
| ***A61K 38/17*** | (2006.01) |
| ***A61K 39/00*** | (2006.01) |
| ***G01R 27/26*** | (2006.01) |
| ***H02M 1/00*** | (2007.01) |

(52) U.S. Cl.

CPC ......... *G01R 19/0053* (2013.01); *G01R 19/00* (2013.01); *G01R 19/0092* (2013.01); *G01R 27/2611* (2013.01); *H02M 1/0009* (2021.05); *A61K 38/1793* (2013.01); *A61K 2039/505* (2013.01); *A61K 2300/00* (2013.01)

(58) Field of Classification Search

CPC ............ G01R 19/0053; G01R 19/0092; G01R 27/2611; G01R 19/00; H02M 1/0009; A61K 2039/505; A61K 2300/00; A61K 38/1793

USPC ........................................................ 324/102

See application file for complete search history.

(56) References Cited

U.S. PATENT DOCUMENTS 8,344,722 B2 1/2013 Harper et al.
8,582,266 B2 11/2013 Bertin et al.
(Continued)

FOREIGN PATENT DOCUMENTS

DE 102004062655 A1 7/2006
DE 60309155 T2 8/2007
(Continued)

OTHER PUBLICATIONS

Office Action, in the German language, from counterpart German Application No. 102023118449.0, dated Jul. 30, 2024, 6 pp.
(Continued)

*Primary Examiner* — Raul J Rios Russo
(74) *Attorney, Agent, or Firm* — Shumaker & Sieffert, P.A.

(57) ABSTRACT

A method for measuring current in a conductor, a current measurement circuit, and a power converter with a current measurement circuit are disclosed. The method includes measuring a current (IL) in a conductor in successive measurement cycles using a current measurement circuit (2). Measuring the current (IL), in each measurement cycle, comprises adjusting a start measurement value of the measurement circuit (2) based on a measurement value obtained in a preceding measurement cycle.

10 Claims, 4 Drawing Sheets

(56) References Cited

U.S. PATENT DOCUMENTS

| | | | | |
|---|---|---|---|---|
| 8,648,586 | B2 | 2/2014 | Singh et al. | |
| 9,594,097 | B2 | 3/2017 | Bogner et al. | |
| 11,002,767 | B2 | 5/2021 | Loccia et al. | |
| 11,137,471 | B2 | 10/2021 | Asam | |
| 11,569,811 | B2 | 1/2023 | Mayer et al. | |
| 11,650,233 | B2 | 5/2023 | Bhargava et al. | |
| 2003/0155930 | A1 | 8/2003 | Thomsen | |
| 2010/0315091 | A1* | 12/2010 | Hartlieb | H02M 1/32 324/509 |
| 2010/0327825 | A1 | 12/2010 | Mehas et al. | |
| 2014/0002037 | A1 | 1/2014 | Babazadeh et al. | |
| 2014/0347024 | A1* | 11/2014 | Rozman | G01R 19/0092 323/234 |
| 2016/0077135 | A1 | 3/2016 | Jockel et al. | |
| 2016/0344289 | A1* | 11/2016 | Kris | H03F 3/45 |
| 2019/0128932 | A1 | 5/2019 | Fernandez et al. | |
| 2020/0386788 | A1 | 12/2020 | Cho et al. | |
| 2021/0006147 | A1* | 1/2021 | Feldtkeller | H02M 1/083 |
| 2021/0389353 | A1 | 12/2021 | Bhargava et al. | |
| 2023/0184813 | A1 | 6/2023 | Neag et al. | |
| 2023/0184817 | A1 | 6/2023 | Djelassi-Tscheck et al. | |
| 2023/0194595 | A1 | 6/2023 | Djelassi-Tscheck et al. | |
| 2024/0006986 | A1* | 1/2024 | Wang | H02M 3/01 |
| 2024/0272209 | A1* | 8/2024 | Guthrie | G01R 19/0092 |

FOREIGN PATENT DOCUMENTS

| | | | |
|---|---|---|---|
| DE | 102006007741 | A1 | 8/2007 |
| DE | 102009044992 | A1 | 4/2011 |
| DE | 102012209499 | A1 | 12/2012 |
| DE | 102013212542 | A1 | 1/2014 |
| DE | 102014003405 | A1 | 9/2015 |
| DE | 102014218708 | A1 | 3/2016 |
| DE | 112018005096 | T5 | 8/2020 |
| DE | 102020131640 | A1 | 12/2021 |
| EP | 1503490 | A1 | 2/2005 |

OTHER PUBLICATIONS

Texas Instruments, "Wide Input Range Synchronous Buck Controller With Analog Current Monitor," LM25117-Q1, Apr. 2011, 45 pp.

Yang et al., "Design of High-side Current Sense Amplifier with Ultra-wide ICMR", 2009 52nd IEEE International Midwest Symposium on Circuits and Systems, IEEE, Aug. 2, 2009, pp. 5-8.

Zhou et al., "Lossless bi-directional current sense circuit for low-voltage high-current DC/DC converters", IECON 2018—44th Annual Conference of the IEEE Industrial Electronics Society, IEEE, Oct. 21, 2018, pp. 1305-1308.

* cited by examiner

CURRENT SENSE CIRCUIT AND CURRENT SENSING METHOD THAT ADJUSTS A START MEASUREMENT VALUE FOR SUCCESSIVE MEASUREMENT CYCLES

This Application claims priority to German Application Number 102023118449.0, filed on Jul. 12, 2023, the entire content of which is incorporated herein by reference.

This disclosure relates in general to current sensing, in particular to current sensing in a power converter such as, for example, a DC-DC converter.

Operating a power converter, such as a switched-mode power converter, may include sensing a current flowing through the power converter during operation. The sensed current may be used to regulate an output voltage or an output current of the power converter, may be used to protect the power converter against an overcurrent, or the like. Sensing the current may include coupling a current sense circuit to a load circuit path through which the current to be sensed flows, or coupling a current sensor circuit to a sense circuit path through which a sense current flows. The sense current may be obtained using a current mirror, a current sense transistor, or the like. The current sense circuit may directly be coupled to the load circuit path or the sense circuit path using a sense resistor, for example, or may indirectly be coupled to the second path using an inductive current sensor, for example.

Due to a switched-mode operation of the power converter, ringing may occur in the current and/or may occur at inputs of the current sense circuit, wherein such a ringing may negatively affect the current sensing. According to a conventional approach, the current sense circuit is only activated during predefined time periods in which ringing is reduced. After activating the current sense circuit it may take a while for the current sense circuit to provide a correct sensing (measurement) result. The settling time between the time instance of activating the current sense circuit and the time instance at which the current sense circuit provides a reasonable sensing result may negatively affect the functionality, such as the current or voltage regulation functionality, of the power converter.

There is therefore a need for an improved current sensing, such as current sensing in a power converter.

One example relates to a method. The method includes measuring a current in a conductor in successive measurement cycles using a current measurement circuit. Measuring the current, in each measurement cycle, includes adjusting a start measurement value of the measurement circuit based on a measurement value obtained in a preceding measurement cycle.

Another example relates to a current measurement circuit configured to measure a current in a conductor in successive measurement cycles. The current measurement circuit is further configured, in each measurement cycle, to adjust a start measurement value based on a measurement value obtained in a preceding measurement cycle.

Examples are explained below with reference to the drawings. The drawings serve to illustrate certain principles, so that only aspects necessary for understanding these principles are illustrated. The drawings are not to scale. In the drawings the same reference characters denote like features.

In the following detailed description, reference is made to the accompanying drawings. The drawings form a part of the description and for the purpose of illustration show examples of how the invention may be used and implemented. It is to be understood that the features of the various embodiments described herein may be combined with each other, unless specifically noted otherwise.

Figure 1:
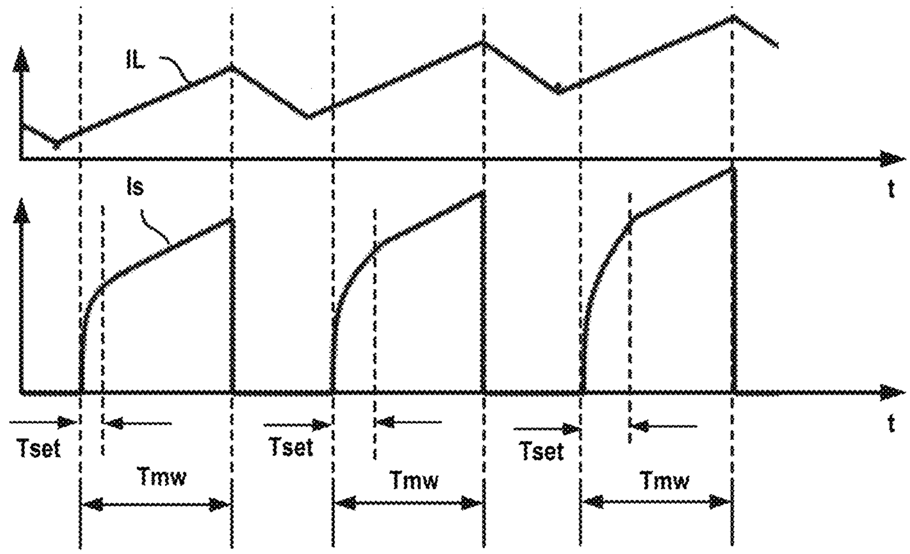
FIG. 1 shows signal diagrams that illustrate a conventional method for measuring a current in successive measurement cycles.

FIG. 1 shows signal diagrams that illustrate a conventional method for measuring a current IL in a conductor in a plurality of successive measurement cycles. In each of these measurement cycles the current in the conductor is measured (sensed) in order to obtain a measurement signal Is that represents the conductor current IL and, in an ideal case, is proportional to the conductor current IL. The conductor current IL is also referred to as load current in the following.

According to one example, the conductor current IL results from a switching process that includes alternatingly switching on and off an electronic switch connected in series with an inductor. The conductor either connects the electronic switch and the inductor, or connects the series circuit including the electronic switch and the inductor to a power source or other devices in an electronic circuit. In this type of switching process, which may typically appear in a power converter, the conductor current IL increases when the electronic switch is in an on-state (switched-on state), and decreases when the electronic switch is in an off-state (switched-off state). Thus, according to one example, the conductor current IL is a current in a power converter, in particular, a current through an inductor in a power converter.

In the method illustrated in FIG. 1, measuring the conductor current IL includes measuring the conductor current IL during those time periods in which the conductor current IL increases. This may include measuring the conductor current IL during those time periods in which the electronic switch is in the on-state. In the method illustrated in FIG. 1, the conductor current IL is measured during measurement windows having a duration Tmw. A measurement cycle includes a measurement window and a pause window following the measurement window, wherein during the pause window measuring the conductor current is interrupted (pauses).

Measuring the conductor current IL and providing the measurement signal Is during the measurement windows includes using a current measurement circuit. In the method according to FIG. 1, the measurement circuit is reset after each measurement window such that at the beginning of a new measurement window the measurement signal Is is zero. The measurement signal then increases to reach a signal value that is representative of the conductor current IL and, for the remainder of the measurement window, tracks the conductor current IL. The higher the conductor current IL, the longer it takes for the measurement signal Is at the beginning of the measurement window to reach a signal value representing the load current IL. A time period between the beginning of a measurement window and the time instance at which the measurement signal Is starts to represent the conductor current IL may be referred to as settling time. Thus, the higher the conductor current IL, the longer the settling time. This is illustrated in FIG. 1, in which the conductor current IL increases over the time, so that from measurement window to measurement window the settling time Tset increases.

Figure 2:
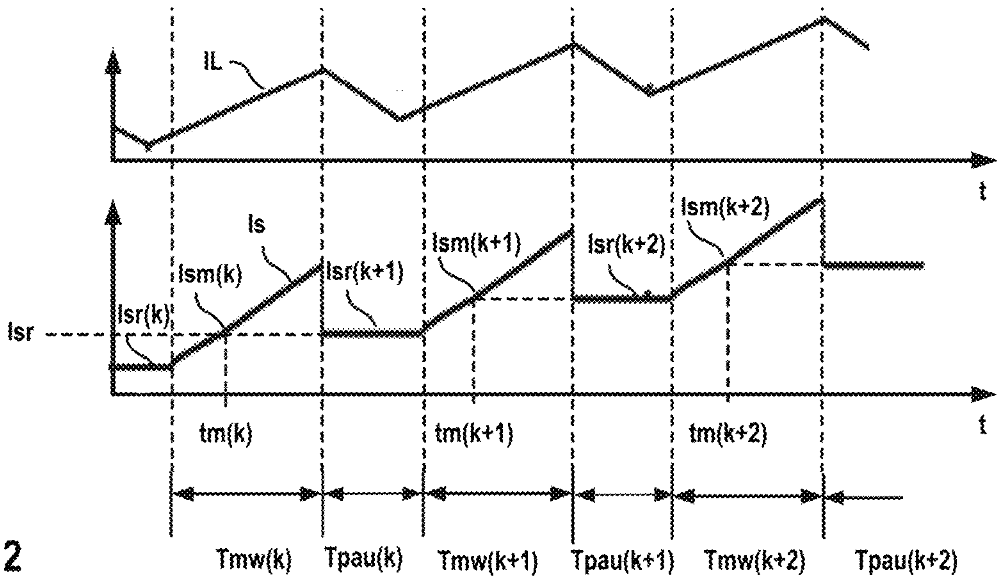
FIG. 2 shows signal diagrams that illustrate one example of a method for measuring a current in successive measurement cycles, wherein the method includes, in each measurement cycle, adjusting a start measurement value based on a measurement value obtained in a preceding measurement cycle.

There is a need for a method for measuring a current through a conductor in a plurality of successive measurement cycles, that each include a measurement window and a pause window following the measurement window, such that measuring the current is as associated with a reduced settling time. FIG. 2 shows signal diagrams that illustrate one example of such method.

More specifically, FIG. 2 shows signal diagrams of a load current IL to be measured and a measurement signal Is that is generated by a measurement circuit (not illustrated in FIG. 2) based on the load current IL. The method according to FIG. 2 includes measuring the load current IL in a plurality of successive measurement cycles. Each measurement cycle includes a measurement window in which the load current IL is measured and a pause window in which measuring the load current IL pauses (is interrupted).

FIG. 2 illustrates three successive measurement cycles, wherein Tmw(k), Tm(k+1), Tmw(k+2) denote durations of the measurement windows and Tpau(k), Tpau(k+1), Tpau (k+2) denotes durations of the pause windows of the measurement cycles. In the following, Tmw denotes durations of the measurement windows in general, and Tpau denotes durations of the pulse windows in general.

Durations Tmw of the measurement windows as well as the durations of the pause windows may vary. That is, the durations Tmw of the measurement windows are not necessarily the same in every measurement cycle, and the durations of the pause windows Tpau between the measurement windows are not necessarily the same in every measurement cycle. Examples for defining the measurement windows and the pause windows are explained herein further below. The durations Tmw of the measurement windows are referred to as measurement durations and the durations Tpau of the pause windows are referred to as pause durations in the following.

The method according to FIG. 2 includes, at the beginning of each measurement window, adjusting a start measurement value of the measurement circuit based on a measurement value obtained in a preceding measurement cycle. A measurement value obtained in a preceding measurement cycle is a measurement value obtained in a measurement window of the preceding measurement cycle. According to one example, in relation to a certain measurement cycle, the preceding measurement cycle is the measurement cycle directly preceding the certain measurement cycle. In this example, the start measurement value at the beginning of the measurement window of the certain measurement cycle based on a measurement value obtained in the measurement cycle that ends at the beginning of the certain measurement cycle. This, however, is only an example. According to another example, there is at least one measurement cycle between the preceding measurement cycle and the certain measurement cycle in which the measurement value from the preceding measurement cycle is used for generating the start measurement value. This is briefly explained in the following.

In the following, Isr denotes the start measurement value in general and Isr(k) denotes the start measurement value of a k-th measurement cycle. Furthermore, Ism(k–i) denotes the measurement value obtained in a preceding measurement cycle (the (k–i)-th measurement cycle) based on which the start measurement value is obtained, so that $$Isr(k) = f(Ism(k-i)), \tag{1}$$

where i is an integer, with i>0, and f(·) is a function that generates the start measurement value Isr (k) based on the measurement value Ism(k–i) obtained in the preceding measurement cycle. In the event that the preceding measurement cycle is the directly preceding measurement cycle, i=1, so that $$Isr(k) = f(Ism(k-1)). \tag{2}$$

According to one example, the start measurement value Isr(k) is proportional to the measurement value obtained in the preceding measurement cycle, so that $$Isr(k) = p \cdot Ism(k-1), \tag{3}$$

where p denotes a proportionality factor. According to one example, the proportionality factor equals one, p=1. In this case, the start measurement value Isr(k) equals the measurement value Ism(k−1) obtained in the preceding measurement cycle.

In FIG. 2, tm(k), tm(k+1), tm(k+2) denote measurement time instances within the measurement windows. At each of these time instances tm(k), tm(k+1), tm(k+2) a measurement value for generating a respective start measurement value may be obtained. According to one example, a measurement value in each measurement window is obtained, and based on the measurement value obtained in one measurement window a start measurement value for the directly succeeding measurement cycle is generated. This, however, is only an example. It is also possible to obtain a measurement value in one measurement window and to generate start measurement values for two or more succeeding measurement cycles based on the measurement value obtained in one measurement window.

According to one example, each of the measurement time instances tm(k), tm(k+1), tm(k+2) is spaced apart from a beginning and an end of the respective measurement window. According to one example, there is a predefined time period between the beginning of the measurement window and the respective measurement time instance tm(k), tm(k+1), tm(k+2). One example for defining the measurement time instances tm(k), tm(k+1), tm(k+2) within the measurement windows is explained herein further below.

As can be seen from FIG. 2, the load current IL may change within the measurement window. Consequently, the measurement signal Is changes within the measurement window. Due to this, the start measurement value not necessarily represents the load current IL at the beginning of a new measurement window. However, in particular in those operating scenarios in which the load current IL is different from zero at the beginning of the individual measurement windows the measurement value obtained in the preceding measurement cycle is a good approximation of the measurement signal at the beginning of a new measurement window, so that the settling time is significantly reduced as compared to the conventional method in which the measurement signal Is starts at zero at the beginning of each new measurement window.

Figure 3:
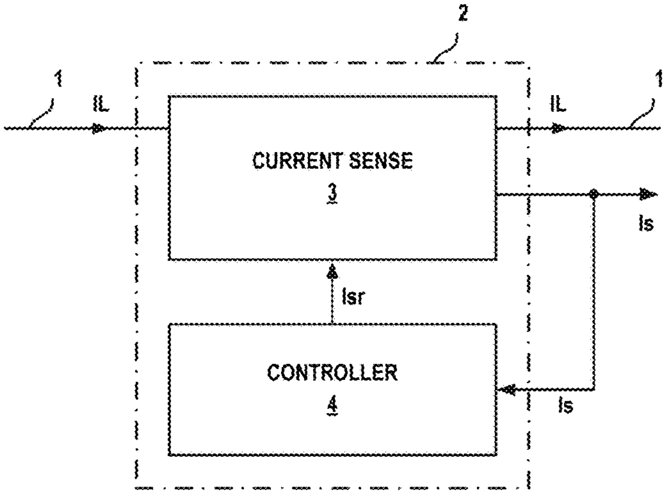
FIG. 3 shows a block diagram of a current measurement circuit according to one example.

FIG. 3 schematically illustrates one example of a measurement circuit 2 that is configured to operate in accordance with the method illustrated in FIG. 2. That is, the measurement circuit according to FIG. 3 is configured to measure a load current IL flowing through a conductor 1 in a plurality of successive measurement cycles and is configured to provide a measurement signal Is that, at least towards an end of each measurement window, represents the load current IL. Referring to FIG. 3, the measurement circuit 2 includes a current sense circuit 3. The current sense circuit 3 is coupled to the conductor 1 and is configured to provide the measurement signal Is. Furthermore, the current measurement circuit 2 includes a controller 4 that is configured to receive the measurement signal Is and provide the start measurement value at the beginning of each new measurement cycle based on a measurement value obtained in a preceding measurement cycle.

The load current IL illustrated in FIG. 3 may be a current flowing through a load (not illustrated in FIG. 3). This, however, is only an example. According to another example, the load current IL sensed by the current measurement circuit 2 is a replica of a current flowing through a load. In this case, the load current IL may be proportional to the current flowing through the load. A load current IL being proportional to the current flowing through a load may obtained using a current mirror, a current sense transistor, or the like.

Figure 4:
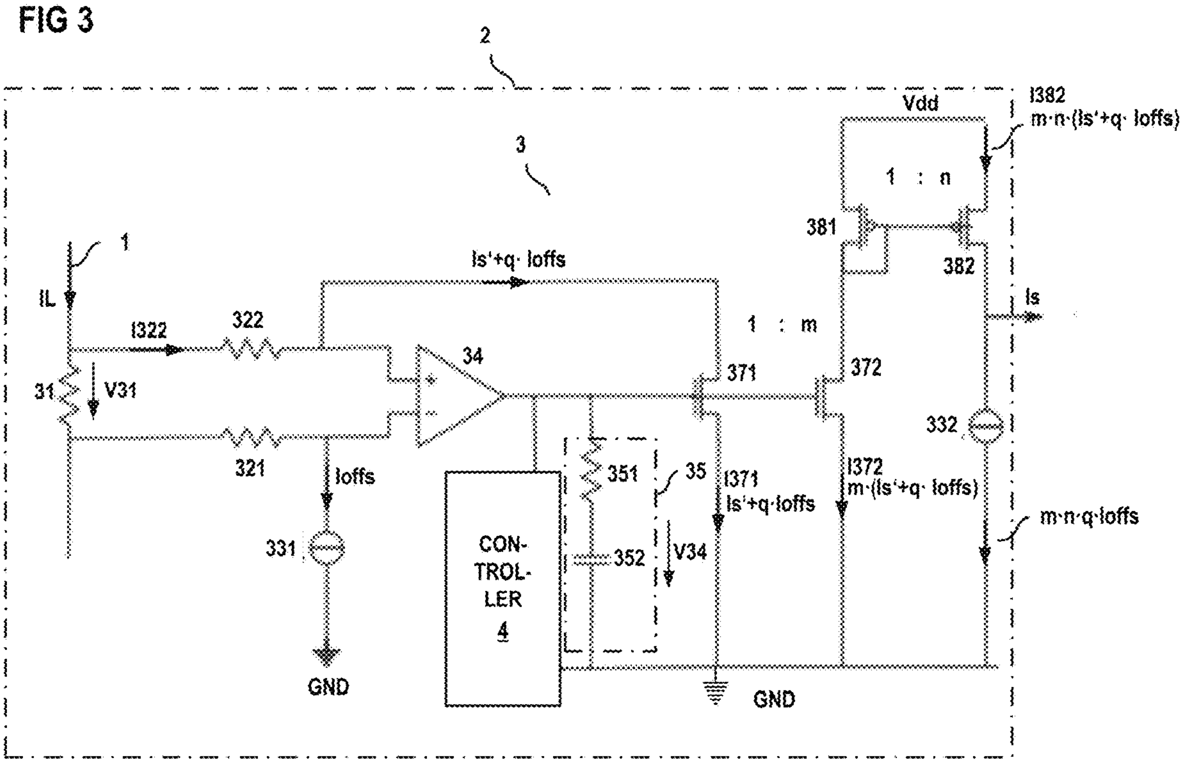
FIG. 4 illustrates one example of a current sense circuit included in the current measurement circuit according to FIG. 3.

FIG. 4 illustrates one example of the current measurement circuit 2 in greater detail. In particular, FIG. 4 illustrates a more detailed example of the current sense circuit 3. The controller 4 is illustrated as a circuit block in FIG. 4. One example of the controller 4 is explained with reference to FIG. 4 herein below.

In the example illustrated in FIG. 4, the current sense circuit 3 includes a shunt resistor 31 connected to the conductor 1 in such a way that the load current IL flows through the shunt resistor 31. A voltage V31 across the shunt resistor 31 is proportional to the load current IL, wherein a proportionality factor between the voltage V31 and the load current IL is given by a resistance R31 of the shunt resistor 31.

The sense circuit 3 further includes an input circuit with an operational amplifier 34, such as an operational transconductance amplifier (OTA), and a first transistor 371 driven by the operational amplifier 34. The operational amplifier 34 drives the first transistor 371 such that a current I371 through the first transistor 371 is given by $$I371 = Is' + q \cdot Ioffs. \tag{4}$$

The current I371 through the first transistor 371 is referred to as first current in the following. Referring to equation (4), the first current I371 includes a first current portion Is' that is proportional to the voltage V31 across the shunt resistor 31, so that the first current portion Is' is proportional to the load current IL, $$Is' \sim IL. \tag{5}$$

A second current portion of the first current I371 equals a known offset q·Ioffs.

Furthermore, the sense circuit 3 includes an output circuit coupled to the first transistor 371. The output circuit includes a second transistor 372 that is driven by the operational amplifier 34 in the same way as the first transistor 371, so that a second current I372, which is a current through the second transistor 372, is proportional to the first current I371, $$I372 = m \cdot I371 = m \cdot (Is' + q \cdot Ioffs), \tag{6}$$

where m is the proportionality factor between the first and second currents I371, I372 and is given by a ratio between a size of the second transistor 372 and a size of the first transistor 371. The output circuit furthermore includes a current mirror with an input transistor 381 connected in series with the second transistor 372 and an output transistor 382 coupled to the input transistor 381. A current I382 through the output transistor 382 is proportional to the current through the input transistor 381 and the current through the second transistor 372, $$I381 = n \cdot I372 = n \cdot m \cdot (Is' + q \cdot Ioffs), \tag{7}$$

where n is a proportionality factor between the output current I382 of the current mirror and the current through the second transistor 372. This proportionality factor n is given by the current mirror ratio of the current mirror. This current mirror ratio is given by a ratio between a size of the output transistor 382 and a size of the input transistor 381.

Referring to FIG. 4, the output current I382 of the current mirror is given by $$I382 = m \cdot n \cdot Is' + m \cdot n \cdot q \cdot Ioffs \tag{8}$$

and includes a first current portion m·n·Is' that is proportional to the load current IL, and a second current portion m·n·q·Ioffs that is proportional to the offset q·Ioffs.

A current source 332 is connected in series with the output transistor 382 of the current mirror and sinks a current that equals the constant second current portion m·n·q·Ioffs of the current mirror output current I382. Thus, at an output of the sense circuit, which is a circuit node between the current mirror output transistor 382 and the current source 332, the current measurement signal Is is available, which is given by $$Is = m \cdot n \cdot Is' \tag{9}$$

and which is proportional to the load current IL.

For driving the first transistor 371 such that the first current I371 is proportional to the voltage V31 across the shunt resistor 31 and the load current IL, a first input of the operational amplifier 34 is connected to a first circuit node of the shunt resistor 31 through a first resistor 321 and a second input of the operational amplifier 34 is connected to a second circuit node (different from the first circuit node) of the shunt resistor 31 through a second resistor 322. Furthermore, a circuit node between the first resistor 321 and the first input of the operational amplifier 34 is connected to an offset current source 331. Furthermore, a second node between the second arrest sister 322 and the second input of the operational amplifier 34 is connected to a load path of the first transistor 371.

Input currents of the operational amplifier 34 are essentially zero, so that a current through the first resistor 321 essentially equals the offset current Ioffs provided by the offset current source 331 and a current through the second resistor 322 essentially equals the first current I371. The operational amplifier 34 drives the first transistor 371 such that a voltage between the input nodes of the operational amplifier 34 is essentially zero. In this case, a voltage V322 across the second resistor 322 is given by a voltage V321 across the first resistor 321 plus the voltage V31 across the shunt resistor V31, $$V322 = V321 + V31. \tag{10a}$$

The voltage V31 across the shunt resistor 31 is given by the load current IL multiplied with the resistance of the shunt resistor 31, and the voltage V321 across the first resistor 321 is given by a resistance R321 of the first resistor 321 multiplied with the offset current Ioffs, so that based on equation (8) the voltage V322 across the second resistor 322 is given by $$V322 = R31 \cdot IL + R321 \cdot Ioffs. \tag{10b}$$

A current I322 through the second resistor 322 is given by the voltage V322 across the second resistor 322 divided by a resistance R322 of the second resistor 322, $$I322 = \frac{V322}{R322}. \tag{11a}$$

Based on equations (10b) and (11a), it can be seen that the current I322 through the second resistor, which equals the first current I371, includes two current portions as follows, $$I322 = I371 = \frac{R31}{R322} \cdot IL + \frac{R321}{R322} \cdot Ioffs = Is' + q \cdot Ioffs. \tag{11b}$$

As can be seen from equation (11b), the proportionality factor between the load current IL and the first current portion of the first current I371 is given by the ratio between the resistance R31 of the shunt resistor 31 and the resistance R322 of the second resistor 322. Furthermore, a proportionality factor q between the offset current Ioffs provided by the offset current source 331 and the second current portion of the first current I371 is given by the ratio between the resistance R321 of the first resistor 321 and the resistance R322 of the second resistor.

According to one example, the first and second resistors 321, 322 have the same resistance, so that R321=R322. Furthermore, the first and second transistors 371, 372 have the same size, so that m=1, and the input transistor 381 and the output transistor 382 of the current mirror have the same size, so that n=1. In this case, the output signal Is equals the first current portion of the first current I371, Is=Is', so that a proportionality factor between the load current IL and the current measurement signal Is is only defined by the resistances R31, R322 of the shunt resistor 31 and the second resistor 322.

Referring to FIG. 4, the sense circuit 3 further includes compensation network 35 connected to the output of the operational amplifier 34. This compensation network 35 includes an RC filter, for example, and may include a series circuit with a resistor 351 and a capacitor 352. The compensation network 35 increases the operating stability of the current measurement circuit 2.

In the current measurement circuit 2 according to FIG. 4, the controller 4 is configured to sense the output voltage V34 at the measurement time instance tm in a preceding measurement cycle; store a measurement value representing the output voltage V34 at the measurement time instance tm; and, at the beginning of a new measurement cycle, adjust the output voltage V34 of the operational amplifier 34 based on the stored measurement value such that the output voltage V34 equals the output voltage V34 at the measurement time instance tm in the preceding measurement cycle. In this way, the measurement signal Is at the beginning of the new drive cycle equals the measurement signal Is at the measurement time instance tm in the preceding drive cycle. The measurement value stored in the controller 4 therefore represents the start measurement value at the beginning of the new drive cycle.

Adjusting the output voltage V34 by the controller 4 at the beginning of the new drive cycle includes adjusting the voltage across the filter 35, which includes charging the capacitor 352 of the filter 35. It should be noted that the controller 4 adjusts the output voltage V34 of the operational amplifier 34 only at the beginning of the new measurement cycle, so that the measurement signal Is has the desired start measurement value. After having pre-charged the capacitor 352 the controller 4 allows the operational amplifier 34 to adjust the output voltage V34 based on the load current IL in order to obtain the corresponding level of the current measurement signal Is.

Figure 5:
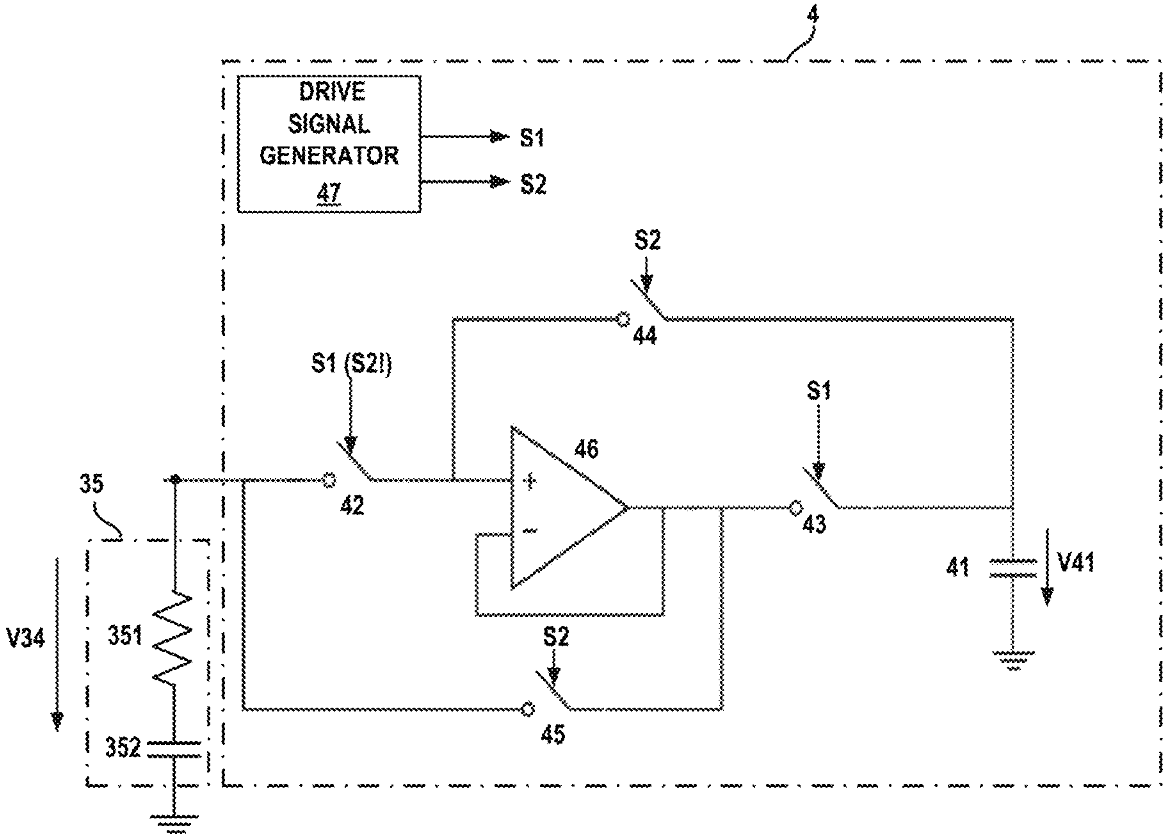
FIG. 5 illustrates one example of a control circuit included in the current measurement circuit according to FIG. 3.
Figure 6:
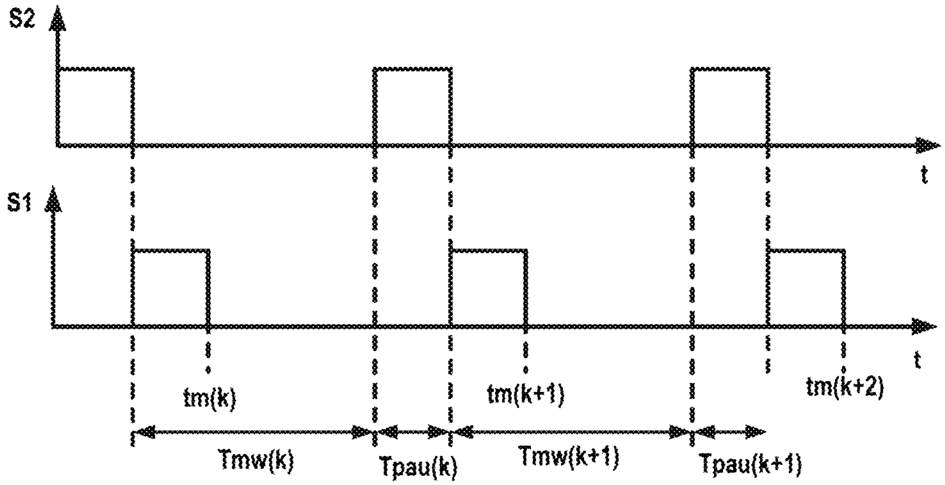
FIG. 6 shows signal diagrams that illustrate one example of operating the control circuit according to FIG. 5.

One example of the controller 4 is illustrated in FIG. 5. Referring to FIG. 5, the controller 4 includes a capacitor 41 configured to store the output voltage V34 of the operational amplifier (not illustrated in FIG. 5) at the measurement time instances, a voltage buffer 46, several switches 42, 43, 44, 45, and a drive signal generator 47 configured to provide drive signals S1, S2 received by the switches 42-45. The drive signal generator 47 may include a microcontroller, a logic signal generator, a finite state machine, or the like. Examples of signal diagrams of the drive signals S1, S2 provided by the drive signal generator 47 are illustrated in FIG. 6.

Referring to FIG. 5, the controller 4 includes a first electronic switch 42 that connects an input of the voltage buffer 46 to the output of the operational amplifier 34 (not illustrated in FIG. 5) and the filter 35, and a second electronic switch 43 that connects an output of the voltage buffer 46 to the capacitor 41. Thus, a voltage V41 across the capacitor 41 tracks the output voltage V34 of the operational amplifier 34 when both the first switch 42 and the second switch 43 are switched on (are in the on-state).

Furthermore, the controller includes a third switch 44 that connects the capacitor 41 to the input of the voltage buffer 46, and a fourth switch 45 that connects the output of the voltage buffer 46 to the filter 35. Thus, the controller 4 adjusts the voltage V34 across the filter 35 to be equal to the voltage V41 across the capacitor 41 when both the third switch 44 and the fourth switch 45 are switched on (are in the on-state).

The operating state of the controller 4 in which the first and second switches 42, 43 are in the on-state, so that the capacitor voltage V41 tracks the operational amplifier output voltage V34, is referred to as first operating state in the following. The operating state of the controller 4 in which the third and fourth switches 44, 45 are in the on-state, so that the operational amplifier output voltage V34 equals the capacitor voltage 41, is referred to as second operating state in the following.

In the example illustrated in FIGS. 5 and 6, the first operating state is governed by a first drive signal S1 that drives the first and second switches 42, 43, and the second operating state is governed by a second drive signal S2 that drives the third and fourth switches 44, 45. Each of the first and second drive signals either has an on-level that switches on the respective switch or an off-level that switches off the respective switch. Just for the purpose of illustration, the on-level is a high signal level in the example illustrated in FIG. 6, and the off-level is a low signal level in the example illustrated in FIG. 6. Thus, the controller 4 is in the first operating state when the first drive signal S1 has a high signal level, and the controller 4 is in the second operating state when the second drive signal S2 has a high signal level.

Referring to FIG. 6, the controller 4 is in the first operating state for a certain time period before a respective measurements time instance tm (wherein tm represents an arbitrary one of the measurements time instances tm(k), tm(k+1), tm(k+2) illustrated in FIG. 6), so that the capacitor voltage V41 tracks the operational amplifier output voltage V34. The first operating state ends at the measurements time instance tm, so that the voltage level of the operational amplifier output voltage V34 at the measurements time instance tm is stored as the capacitor voltage. Just for the purpose of illustration, in the example illustrated in FIG. 6, the first operating state starts at the beginning of the measurement window Tmw (wherein Tmw represents an arbitrary one of the measurement windows Tmw(k), Tmw(k+1), Tmw(k+2) illustrated in FIG. 6). This, however, is only an example. It is also possible to start the first operating state after the beginning of the measurement window but before the measurement time instance.

Referring to FIG. 6, the controller 4 is in the second operating state for a certain time period before the beginning of a new measurement cycle, so that a voltage corresponding to the capacitor voltage V41 is provided to the filter 35 and, therefore, the first transistor 371 by the controller 4. The voltage stored by the capacitor 41 and provided to the filter 35 and the first transistor 371 at the beginning of the new measurement cycle results in the start measurement value of the current measurement signal Is. The second operating state, in which the voltage V34 across the filter 35 is provided by the controller 4, ends at the beginning of the new measurement cycle, so that the measurement circuit 2 can start to track the load current IL. Just for the purpose of illustration, in the example illustrated in FIG. 6, the controller 4 is in the second operating state during the pause periods Tpau(k), Tpau(k+1), Tpau(k+2). This, however, is only an example. It is also possible to operate the controller 4 in the second operating state for time periods shorter than the pause periods Tpau(k), Tpau(k+1), Tpau(k+2) and each ending with a respective new measurement cycle.

In the example illustrated in FIGS. 5 and 6, the first and second switches 42, 43 are driven by the first signal S1, so that both switches 42, 43 are in the same operating state at each time. This, however, is only an example. According to another example, the third switch 43 is driven by the first drive signal S1, that defines the first operating state, and the second switch 42 is driven by the negated (inverted) second drive signal S2! (as indicated in brackets in FIG. 5), so that the first switch 42 is switched on each time the controller 4 is not in the second operating state.

Figure 7:
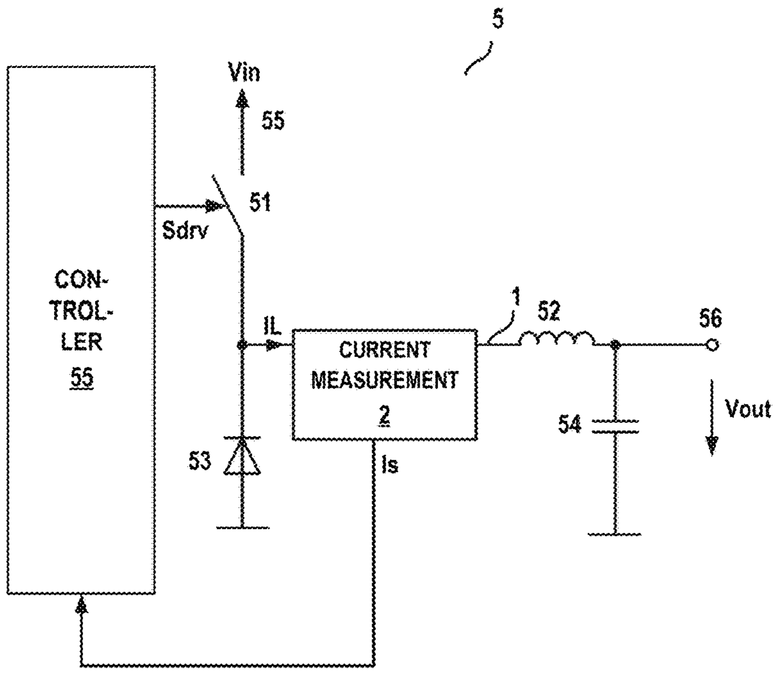
FIG. 7 shows one example of a power converter that includes a current measurement circuit.

FIG. 7 illustrates one example of a power converter that includes a current measurement circuit 2 operating in accordance with the method illustrated in FIG. 2. According to one example, the current measurement circuit 2 is implemented in accordance with any of the examples explained with reference to FIGS. 3 to 6. The power converter includes an electronic switch 51 and an inductor 52 connected in series with the electronic switch 51. The electronic switch 51 is connected to a supply node 55 for receiving an input voltage Vin, and the inductor 52 is connected to an output node 56, wherein output voltage Vout is provided.

The conductor 1, in which the load current IL is measured by the current measurement circuit 2, connects the electronic switch 51 and the inductor 52. This, however, is only an example. It is also possible to measure the load current IL between the supply node and the electronic switch 51, or between the inductor 52 and the output 56.

For the purpose of illustration, the power converter illustrated in FIG. 7 is a buck converter. In addition to the switch 51 and the inductor 52, the buck converter includes a controller 55 configured to control operation of the electronic switch 51, an output capacitor 54 across which the output voltage Vout is available, and a freewheeling element 53, such as a diode 53 connected in parallel with a series circuit including the inductor 52 and the output capacitor 54. Implementing the power converter as a buck converter, however, is only an example. The current measurement circuit 2 may be used in any other type of power converter as well. Such other type of power converters include, but are not restricted to, a boost converters, flyback converters, buck-boost converters, Sepic converters, Cûk converters, or the like.

In a conventional way, the power converter 5 according to FIG. 7 is configured to regulate one of the output voltage Vout or an output current Iout by a switched-mode operation of the electronic switch 51. For this, the controller 55 receives an output signal Sout, which represents the instantaneous signal level of the output voltage Vout or the output current Iout, whichever is to be regulated.

Referring to FIG. 7, which shows signal diagrams of a drive signal Sdrv driving the electronic switch 51, the load current IL, and the current measurement signal Is, the load current IL increases when the electronic switch 51 is in the on-state and decreases when the electronic switch 51 is in the off-state. When the electronic switch 51 is in the off-state, the freewheeling element 53 takes over the load current IL through the inductor 52.

Figure 8:
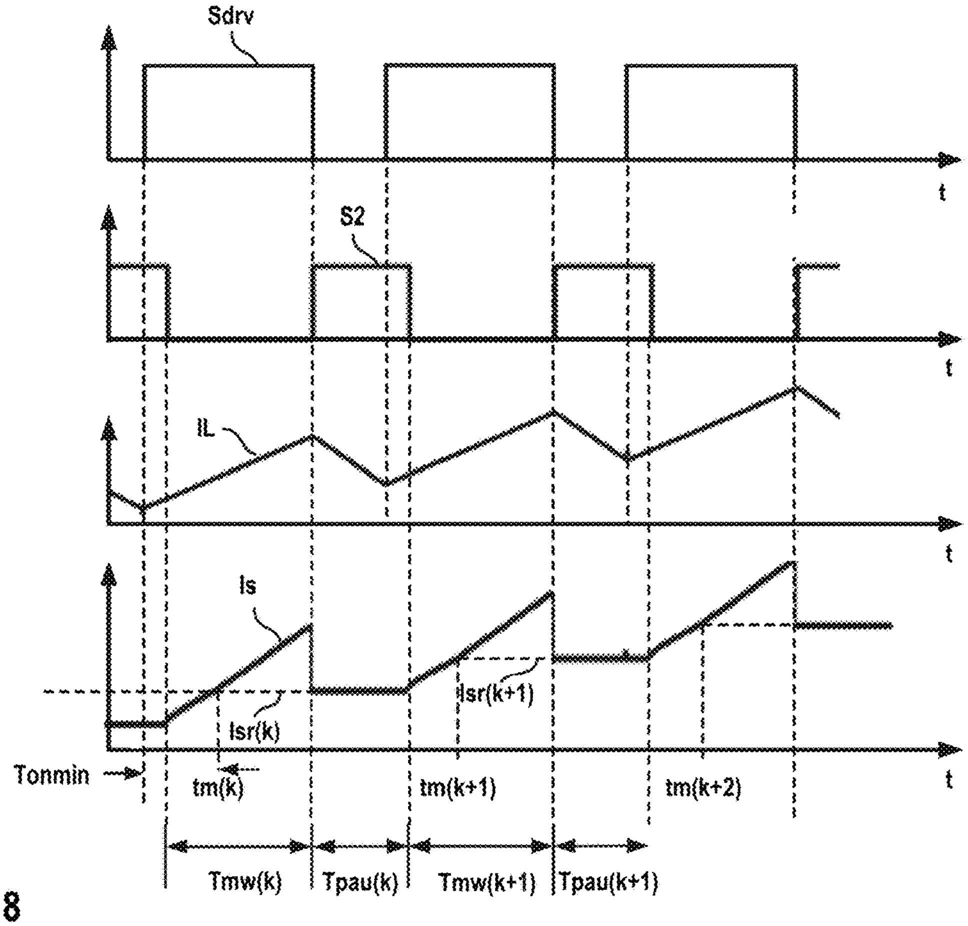
FIG. 8 shows signal diagrams that illustrate operation of the power converter and the current measurement circuit included in the power converter according to FIG. 7.

In the example illustrated in FIG. 8, generating the current measurement signal Is includes generating the current measurement signal Is such that the current measurement signal Is during the pause period Tpau after a measurement window and before a new measurement window essentially equals the measurement value obtained at the measurement time instance tm during the measurement window, so that the start measurement value Isr at the beginning of the new measurement window equals the measurement value. FIG. 8 illustrates three successive measurement cycles. A start measurement value at the beginning of the measurement time window Tm(k+1) of a second measurement cycle, for example, equals the measurement value Isr(k) obtained at the measurement time instance tm(k) in the measurement time window Tm(k) of a first measurement cycle. In a measurement circuit 2 having a controller 4 of the type illustrated in FIG. 6, this can be achieved by operating the controller 4 in the second operating state throughout the pause periods Tpau(k), Tpau(k+1), Tpau(k+2). For this example, the drive signal S2 governing the second operating state of the controller 4 is also illustrated in FIG. 8.

According to one example, the second drive signal S2 is generated such that the second operating state of the controller 4 starts when the electronic switch 51 switches off, that is, when a signal level of the drive signal Sdrv changes from an on-level (that switches on the switch 51) to an off-level (that switches off the switch 51). The second operating state of the controller 4 ends after the beginning of a new drive cycle, that is, after the electronic switch 51 has been switched on for the next time. A delay time between the time instance when the Sdrv changes from the off-level to the on-level in order to switch on the electronic switch 51 and the beginning of the new measurement window may be selected such that voltage oscillations (voltage noise), which may occur after switching on the electronic switch 51, have decayed when the new measurement window starts. According to one example, the controller 55 is configured to generate the drive signal Sdrv such that the drive signal has the on-level at least for a certain time period Tonmin, which may be referred to as minimum on-time. According to one example, the delay time between the time instance when the drive signal Sdrv changes to the on-level and the beginning of the measurement window equals the minimum on-time Tonmin. In this example, the same signal can be used to define the minimum on-time of the electronic switch 51 and the delay time between the beginning of a new drive cycle of the electronic switch 51 and the beginning of the measurement window.

In the example illustrated in FIG. 7, the current measurement circuit 2 is directly coupled to the conductor 1 connecting the electronic switch 51 and the inductor 52, so that the load current IL measured by the current measurement circuit 2 is the current through the inductor 52. This, however, is only an example. It is also possible to include a current path in the power converter through which a replica of the current through the inductor 52 flows, and to measure the replica of the inductor current. Such replica of the inductor current may be obtained by implementing the electronic switch 51 as a transistor circuit with a load transistor and a sense transistor. The load transistor conducts the current that flows through the inductor 52, and the sense transistor provides a sense current that is essentially proportional to the load current. The sense current may be measured by the current measurement circuit 2 in order to obtain the current measurement signal Is. A transistor arrangement with a load transistor and a sense transistor is commonly known, so that no further explanation is required in this regard.

Briefly summarizing what is explained herein before, one example relates to a method that includes measuring a current in a conductor in successive measurement cycles using a current measurement circuit. Measuring the current, in each measurement cycle, includes adjusting a start measurement value of the measurement circuit based on a measurement value obtained in a preceding measurement cycle.

The start measurement value may be obtained in the preceding measurement cycle at a time instance that is different from a beginning of the preceding measurement cycle and that is different from an end of the preceding measurement cycle.

According to one example, measuring the current includes measuring the current in a power converter that includes at least one electronic switch. Each of the measurement cycles may be during an on-time of the at least one electronic switch and may be shorter than the on-time of the at least one electronic switch. The at least one electronic switch may have a minimum on-time, and the start measurement value may be obtained at a time instance when the minimum on-time of the at least one electronic switch expires. According to one example, the power converter is one of a buck converter, a boost converter, a buck-boost converter, a flyback converter, or a Sepic converter.

Another example relates to a current measurement circuit configured to measure a current in a conductor in successive measurement cycles. The current measurement circuit is further configured, in each measurement cycle, to adjust a start measurement value based on a measurement value obtained in a preceding measurement cycle.

According to one example, the current measurement circuit is configured to obtain the start measurement value in the preceding measurement cycle at a time instance that is different from a beginning of the preceding measurement cycle and that is different from an end of the preceding measurement cycle.

The current measurement circuit may be included in a power converter. Thus, another example relates to a power converter that includes at least one electronic switch, a control circuit configured to control operation of the at least one electronic switch, and the current measurement circuit. The current measurement circuit is configured to measure a current in a conductor of the power converter and provide a current measurement signal based on the measured current to the control circuit.

In the power converter, the control circuit maybe configured to operate the at least one electronic switch in a plurality of successive drive cycles each including a minimum on-time, wherein the current measurement circuit may be configured to obtain the start measurement value at a time instance at which the minimum on-time in each of the plurality of successive drive cycles expires.

The invention claimed is:

1. A method, comprising:

measuring a current in a conductor in successive measurement cycles using a current measurement circuit to generate a current measurement signal, wherein measuring the current, in each of the successive measurement cycles, comprises adjusting a start measurement value of the current measurement signal at a beginning of the measurement cycle based on a measurement value of the current measurement signal obtained in a preceding measurement cycle.

2. The method of claim 1, wherein the start measurement value is obtained in the preceding measurement cycle at a time instance that is different from a beginning of the preceding measurement cycle and that is different from an end of the preceding measurement cycle.

3. The method of claim 1, wherein measuring the current comprises measuring the current in a power converter that includes at least one electronic switch.

4. The method of claim 3, wherein each of the successive measurement cycles is during an on-time of the at least one electronic switch and is shorter than the on-time of the at least one electronic switch.

5. The method of claim 4, wherein the at least one electronic switch has a minimum on-time, and wherein the start measurement value is obtained at a time instance when the minimum on-time of the at least one electronic switch expires.

6. The method of claim 3, wherein the power converter is selected from the group consisting of:

a buck converter;

a boost converter;

a buck-boost converter;

a flyback converter; and a Sepic converter.

7. A current measurement circuit configured to measure a current in a conductor in successive measurement cycles and generate a current measurement signal, wherein the current measurement circuit is further configured, in each of the successive measurement cycles, to adjust a start measurement value of the current measurement signal at a beginning of the measurement cycle based on a measurement value of the current measurement signal obtained in a preceding measurement cycle.

8. The current measurement circuit according to claim 7, wherein the current measurement circuit is configured to obtain the start measurement value in the preceding measurement cycle at a time instance that is different from a beginning of the preceding measurement cycle and that is different from an end of the preceding measurement cycle.

9. A power converter, comprising:

at least one electronic switch;

a control circuit configured to control operation of the at least one electronic switch; and a current measurement circuit configured to measure a current in a conductor of the power converter in successive measurement cycles and provide a current measurement signal based on the measured current to the control circuit, wherein the current measurement circuit is further configured, in each of the successive measurement cycles, to adjust a start measurement value of the current measurement signal at a beginning of the measurement cycle based on a measurement value of the current measurement signal obtained in a preceding measurement cycle.

10. The power converter of claim 9, wherein the control circuit is configured to operate the at least one electronic switch in a plurality of successive drive cycles each including a minimum on-time; and wherein the current measurement circuit is configured to obtain the start measurement value at a time instance at which the minimum on-time in each of the plurality of successive drive cycles expires.

* * * * *